United States Patent [19]

Zamek et al.

[11] Patent Number: 4,607,103
[45] Date of Patent: Aug. 19, 1986

[54] METHODS FOR MAKING BLOCKED ISOCYANURATES

[75] Inventors: Otto S. Zamek; Richard J. Stein, both of Schenectady, N.Y.

[73] Assignee: General Electric Company, Silicone Products Division, Waterford, N.Y.

[21] Appl. No.: 765,305

[22] Filed: Aug. 13, 1985

[51] Int. Cl.$^4$ .................................... C07D 251/34
[52] U.S. Cl. ............................................. 544/193
[58] Field of Search ................................... 544/193

[56] References Cited

U.S. PATENT DOCUMENTS

| | | | |
|---|---|---|---|
| 2,952,665 | 9/1960 | Bunge et al. | 544/221 |
| 4,246,132 | 1/1981 | Gras et al. | 544/193 |
| 4,255,569 | 3/1981 | Muller et al. | 544/193 |
| 4,306,051 | 12/1981 | Gras et al. | 544/193 |

Primary Examiner—John M. Ford

[57] ABSTRACT

There is provided a method for making blocked isocyanate trimers comprising (A) blocking at least one organic diisocyanate with at least one blocking compound, such as a monohydroxy compound and thereafter (B) heating the reaction product of step (A) in the presence of a catalyst having the general formula

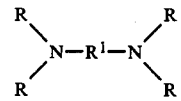

where each R is independently selected from hydrogen and lower alkyl radicals and $R^1$ is an alkylene radical having up to about six carbon atoms; for an amount of time effective for forming blocked isocyanate trimers.

22 Claims, No Drawings

METHODS FOR MAKING BLOCKED ISOCYANURATES

BACKGROUND OF THE INVENTION

The present invention relates to blocked isocyanates and methods for making the same. More particularly, the present invention relates to methods for making blocked isocyanates which utilize a more effective catalyst than was available in the prior art. Blocked isocyanates prepared by the method of the present invention contain substantially less undesired byproducts in the reaction product than was heretofore possible.

Organic polyisocyanates and especially the diisocyanates are commercially important both as starting materials for a number of resins and as crosslinking agents for polymer systems having reactive hydrogen-containing groups; e.g. alcohols, aldehydes, amines, amides and the like. When isocyanates are to be used as crosslinking agents, the highly reactive isocyanate groups are frequently deactived by blocking until crosslinking is to be effected. Blocked isocyanates can be prepared by reacting the isocyanate moiety with a monofunctional compound such as an alcohol to form the corresponding urethane. At high temperatures, for example, in a wire tower, the urethane unblocks, liberating the starting alcohol and regenerating the free isocyanate groups which can be used to crosslink the wire enamel polymer system.

Bunge et al., U.S. Pat. No. 2,952,665, discloses that cyclic trimers of diisocyanates containing three blocked isocyanato groups can be prepared by reacting an organic diisocyanate with a monohydroxy compound and thereafter adding a tertiary amine catalyst at temperatures of at least about 150° C. Representative tertiary amines suitable for use as a catalyst include dimethyl aniline, hexahydrodimethylaniline, 4-methyl morpholine, 4-ethyl morpholine, permethylated diethylene triamine or triethylene tetramine, urethanes consisting of 1 mol of N,N-dialkylaminoethanol and 1 mol of phenyl isocyanate or cyclohexyl isocyanate, N-dialkyl piperazine and N,N'-dimethylethanolamine. Consideration of the examples reveals that anywhere from 5 to 25 hours of heating at temperatures of at least 150° C. is necessary, depending upon the particular reactants, the catalyst and the amount of catalyst employed to obtain a blocked isocyanate.

It has now been discovered that amines having the general formula

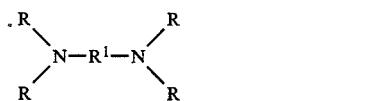
(I)

where each R is independently selected from hydrogen and lower alkyl radicals and $R^1$ is an alkylene radical having up to about six carbon atoms, are more effective as catalysts than any of the amines disclosed by the prior art. Tetramethylethylenediamine has been found to be especially effective as a catalyst. Quite unexpectedly, the use of tetraalkylated alkylene diamines of Formula I allows the artisan to effect trimerization of isocyanato molecules at much lower temperatures in a comparable amount of time, or at elevated temperatures, such as employed by Bunge et al., in a substantially shorter period of time. It has also surprisingly been found that compositions prepared according to the present method, especially at temperatures less than about 120° C., contain less undesired by-products than obtained in prior art methods.

SUMMARY OF THE INVENTION

It is an object of the present invention to provide an improved method for preparing blocked isocyanates.

It is another object of the present invention to provide a method for preparing blocked isocyanates which utilizes tetraalkylated alkylene diamines as catalyst.

Still another object of the present invention is to provide blocked isocyanates prepared by the process of the present invention.

In accordance with one aspect of the present invention there is provided a method for making blocked isocyanate trimers comprising:

(A) blocking
 (1) one of the functional groups of an organic diisocyanate with
 (2) at least one blocking compound and, thereafter
(B) heating the reaction product of (A) in the presence of
 (3) a catalyst having the general formula

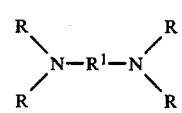

where each R is independently selected from hydrogen and lower alkyl radicals and $R^1$ is an alkylene radical having up to about six carbon atoms; for an amount of time effective for forming blocked isocyanate trimers.

Preferably the catalyst is tetramethylethylenediamine and the reaction is carried out at a temperature of from about 80° C. to about 120° C., and more preferably at a temperature of from about 90° C. to about 100° C. It is also preferred that the blocked isocyanate be prepared via a two step reaction comprising blocking one of the isocyanato groups of the organic diisocyanate and thereafter adding an amount of catalyst effective for promoting trimerization. Generally, it is desirable to employ a polar organic solvent free of active hydrogen atoms and having a boiling point of at least 90° C., for example Cellosolve acetate, butyl acetate, and the like.

DESCRIPTION OF THE INVENTION

The present invention provides a method for making blocked isocyanate trimers comprising (A) reacting
 (1) one of the functional groups of an organic diisocyanate with
 (2) at least one blocking compound and, thereafter
(B) heating the reaction product of (A) in the presence of
 (3) a catalyst having the general formula

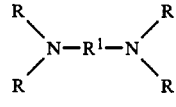

where each R is independently selected from hydrogen and lower alkyl radicals and $R^1$ is an alkylene radical having up to about six carbon atoms; for an amount of time effective for forming blocked isocyanate trimers.

Any suitable organic diisocyanate may be used in the practice of the present invention including, for example, 1-alkylbenzene-2,4-diisocyanate, 1-alkylbenzene-2,5-diisocyanate, 1-alkylbenzene-2,6-diisocyanate, hexamethylene diisocyanate, diphenylmethane-4,4'-diisocyanate, dicyclohexyl methane diisocyanate, phenylenediisocyanate, cyclohexamethylenediisocyanate, 2,6-dialkylbenzene-1,4 diisocyanate, xylenediisocyanate and the like.

Included among the suitable organic diisocyanates are substituted diisocyanates wherein the substituent does not interfere with the reactivity of the isocyanate group. Illustrative of such diisocyanates are 3,3'-dimethoxydiphenylmethane-4,4' diisocyanate, 1-chlorobenzene-2,4-diisocyanate, 1-nitrobenzene-2,4-diisocyanate, 1-alkoxybenzene-2,4-diisocyanate and the like.

Preferably, the organic diisocyanates are selected from the group consisting of 1-alkylbenzene-2,4-diisocyanate, 1-alkylbenzene-2,5-diisocyanate, 1-alkylbenzene-2,6-diisocyanate, hexamethylene diisocyanate, diphenyl methane-4,4'-diisocyanate and dicyclohexyl methane diisocyanate. Toluene diisocyanates are the most preferred diisocyanates for use in the present invention.

If desired, it is possible to produce products with the same degree of polymerization but with a lesser content of blocked isocyanate groups by including calculated amounts of monoisocyanates. The concurrent use of monoisocyanates leads to cyclic trimers, in the form of an isocyanaurate ring from three isocyanato groups, one or two of them derived from the monoisocyanate molecule and the remaining derived from the diisocyanate molecules. The artisan will readily appreciate that such a trimer has one or two side chains which contain no functional groups at all because of the monoisocyanate used in its formation. Phenyl isocyanate is particularly suitable for this purpose.

The organic diisocyanates or their mixtures are preferably blocked by reaction with monohydroxy compounds so as to form relatively stable urethane moieties. Included among the suitable monohydroxy compounds are phenol, cresols, xylenols and aliphatic or cycloaliphatic alcohols. Preferably, the alcohols used in the practice of the invention contain at least about four carbon atoms and, more preferably, are branched alcohols such as t-butanol and sec-butanol. Substituted hydroxy compounds such as nitrophenol and the like can also be employed provided the substituted group does not interfere with the reaction of the diisocyanate and the monohydroxy compound. Phenol is the most preferred monohydroxy blocking compound.

In the reaction of the organic diisocyanates with hydroxy compounds, either some or all of the isocyanate groups present are transformed into the corresponding urethane groups, depending upon the proportions used. It is preferable to use the components in a mole ratio of diisocyanate to monohydroxy compound of from 1:0.6 to 1:1.5, with a particularly advantageous ratio being about 1:1.

It is, of course, also possible to use mixtures of different monohydroxy compounds such as mixtures of phenol and t-butanol.

The monohydroxy compound used as a blocking agent can be used to regulate the unblocking temperature—i.e., the temperature at which free isocyanate groups for crosslinking are regenerated. In the current work it has been found that phenol, cresols and cyclohexanol will provide the most desirable unblocking temperatures. When linear aliphatic monohydroxy compounds are used for blocking, the unblocking temperature will be somewhat higher due to the increased stability of the urethane. For specific uses the higher unblocking temperature may be found to be desirable.

In addition to the monohydroxy blocking compounds, it is also possible to utilize lactams, caprolactams and the like as blocking agents, however, the use of such compounds as blocking agents may introduce solubility problems.

Amine catalysts for use in practicing the present invention have the general formula

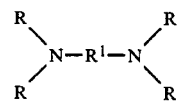

where each R is independently selected from hydrogen and lower alkyl radicals and $R^1$ is an alkylene radical having up to about six carbon atoms. Preferably, R is methyl, ethyl, propyl or a mixture thereof. As the number of carbon atoms present in the R groups increases, the compound's effectiveness as a catalyst decreases, hence it is preferable that all of the R groups be methyl. $R^1$ can be any alkylene radical having up to six carbon atoms, however, it is preferred that $R^1$ have from two to four carbon atoms. Most preferably $R^1$ is ethylene. Consequently, the most preferred catalyst for practicing the present invention is tetramethylethylenediamine.

These catalysts have been found to be particularly effective for promoting trimerization of diisocyanates having one of their isocyanate groups blocked. Generally, an effective amount of catalyst can be from about 0.05% to about 5% by weight based on the weight of organic diisocyanate and blocking compound. Preferably, the amount of catalyst is from about 0.10% to about 0.50% by weight based on the weight of diisocyanate and blocking agent.

Optionally, but preferably, reaction is conducted in a suitable solvent. This is especially true of the trimerization reaction. Generally, suitable solvents are polar organic solvents free of active hydrogen atoms and having a boiling point greater than about 90° C. or the temperature at which the reaction is carried out, whichever is higher. Suitable solvents include DuPont ®DBE which is a blend of the dimethyl esters of succinic, glutaric and adipic acids, Cellosolve acetetate, butyl acetate and the like. Other suitable solvents can readily be ascertained without undue experimentation. DuPont DBE is particularly preferred.

At lower temperatures, e.g. 80° C. to 120° C., it is preferable to include a catalyst for promoting the blocking reaction. Suitable catalysts are well known in the art and include amines and metal salts of carboxylic acids such as dibutyltin dilaurate and the like.

There are two general routes available for making blocked isocyanates in accordance with the present invention. The preferred method is a block-and-trimerize process whereby the blocking agent, preferably a monohydroxy compound, is slowly added to a heated solution of organic diisocyanate. The monohydroxy compound reacts almost immediately with one of the isocyanate groups of the organic diisocyanate to form a urethane moiety, thereby blocking the isocyanate from reacting further. This reaction is exothermic so the rate of addition of monohydroxy compound must be regulated to keep the reaction under control. Generally, the blocking reaction can be carried out at temperatures ranging from about 80° C. to about 160° C. Preferably, such blocking reaction is carried out at a temperature of from about 90° C. to about 120° C.

After the monohydroxy compound has completely reacted, inert solvent and trimerization catalyst are added and the mixture stirred at a temperature of from about 80° C. to about 175° C. until trimerization is complete. Preferably, the trimerization reaction is effected at a temperature of from about 90° C. to about 120° C. and, more preferably, at a temperature ranging from about 90° C. to about 100° C. The advantage of using a lower trimerization reaction temperature is that the reaction product contains less undesired by-products and provides more reaction leeway. Reaction leeway is the time available after the reaction is substantially complete but before it has proceeded too far and becomes essentially unusuable due to gelation and the like.

It should be noted that the solvent insures a homogeneous solution and minimizes the viscosity increase that takes place as the reaction proceeds. As previously pointed out, it is essential that the solvent not react with the free isocyanate groups of the organic diisocyanate. However, such a solvent can be added subsequent to trimerization if so desired.

The trimerization reaction is the more critical of the two and shows greater temperature sensitivity. This fact is illustrated by the amount of reaction leeway available at different trimerization temperatures (see examples). Trimerization will not occur at lower temperatures without the catalysts of the present invention and occurs much more rapidly at the elevated temperatures taught by the prior art.

Blocked isocyanates prepared according to this method have exhibited shelf lives in excess of three months.

An alternate and less preferred method for preparing the blocked isocyanates of the present invention involves first trimerizing the organic diisocyanate and thereafter blocking the free isocyanate groups with a blocking agent such as a monohydroxy compound. This method is more difficult since it requires trimerizing the difunctional molecule. Moreover, the trimerized material is extremely reactive and tends to form higher molecular weight material by reaction of the free isocyanate groups present. Consequently, it is important to use very mild conditions when this method is employed.

The blocked isocyanates of the present invention may be used as a crosslinking agent in polymer systems having reactive hydrogen-containing groups such as alcohols, aldehydes, amides and the like.

In carrying out the crosslinking reaction, the components (e.g. polymer and crosslinking agent) are heated to a temperature at which the blocked isocyanate is converted to the underlying free isocyanate. In most cases, temperatures above about 140° C. are effective to split off the blocking hydroxy compound with formation of the free isocyanate. Once the free isocyanate is formed it immediately reacts with the polymer (typically a polyhydroxy compound). The isocyanurate ring formed by the trimerization reaction is stable not only against the temperature used for splitting off the blocking compound, but even against temperatures in excess of 300° C.

The invention is further illustrated by the following examples in which all parts and percentages are by weight unless otherwise noted.

EXAMPLES

EXAMPLE 1

A clean dry flask equipped with a mechanical stirrer, heating mantle, thermometer, nitrogen inlet and reflux condenser was charged with 200 parts by weight of toluene diisocyanate and heated to 90° C. Next, 118.9 parts by weight of phenol were slowly added over the course of one hour and fifteen minutes and the temperature thereafter maintained at 90° for an additional two hours. At this time 319 parts by weight Dupont ®DBE solvent and 0.8 parts by weight tetramethylethylenediamine catalyst were added. After nine hours at 90° C. the trimerization reaction was complete. The reaction product was clear and had a viscosity of 8970 centistokes at 25° C. The reaction leeway time in this example was two hours.

EXAMPLES 2–4

Example 1 was repeated except that the blocking reaction was carried out at 160° C. for 2.5, 2.25 and 2 hours for Examples 2, 3 and 4, respectively. The trimerization reaction temperature and time were varied. The results are set forth in Table I.

TABLE I(1)

| Ex | Blocking Temperature | Trimerization Temperature | Trimerization Reaction Time | Reaction Leeway |
|----|----------------------|---------------------------|-----------------------------|-----------------|
| 1  | 90° C.  | 90° C.  | 9.0 hr. | 2.0 hr. |
| 2  | 160° C. | 175° C. | 1.0 hr. | 0.5 hr. |
| 3  | 160° C. | 140° C. | 1.5 hr. | 0.5 hr. |
| 4  | 160° C. | 100° C. | 3.0 hr. | 1.0 hr. |

(1)All reactions were run with the same level of catalyst and solvent.

EXAMPLES 5–9

In these examples, the process of example 1 was repeated except that different potential catalysts were substituted for the tetramethylethylenediamine. The results are set forth in Table II.

TABLE II

| Ex | Catalyst | Trimerization Reaction Time at 90° C. | Results |
|----|----------|---------------------------------------|---------|
| 5 | dibutyltin dilaurate | 6 | failed |
| 6 | N—ethyl morpholine | 8 | failed |
| 7 | triethylamine | 17 | failed |
| 8 | hexamethylene tetramine | 12 | failed |
| 9(1) | tetramethylethylenediamine | 9 | excellent |

(1)When no trimer was formed in example 8 after 12 hours, tetramethylethylenediamine was added to the reaction mass of example 8 and heating continued for 9 hours at which time a trimerized blocked product suitable for use as a crosslinking agent was obtained.

EXAMPLE 10

In this example, the blocked isocyanate trimer prepared in example 1 was used as a crosslinking agent in Alkanex ® polyester wire enamel in place of Mondur ®SH crosslinking agent. The enamel was applied to 18 AWG copper wire in seven passes on a 15 foot vertical tower. The properties of the cured enamel were compared to the same enamel prepared with Mondur SH crosslinking agent. The results are set forth in Table III.

TABLE III

|  | Control | | Example 10 | |
|---|---------|---|------------|---|
| Speed (ft/min) | 50 | 60 | 50 | 60 |
| Surface | B+ | B+ | B+ | B+ |

TABLE III-continued

|  | Control |  | Example 10 |  |
|---|---|---|---|---|
| Continuity (Bks/200 ft) | 0 | 0 | 0 | 0 |
| Flexibility (25%+) | 1X | 1X | 1X | 1X |
| Dissipation Factor (at 170° C.) | 8.3 | 21.8 | 10.7 | 28.4 |
| Thermoplastic Flow | 261 | 267 | 259 | 269 |
| Heat Shock (0%-30 min. @ 155° C.) | 3X | 3X | 3X | 3X |
| Dielectric (KV) | 12.3 | 9.9 | 11.3 | 11.3 |
| Heat Age (0% 100 hrs. @ 175° C.) | 1X | 1X | 1X | 1X |
| Repeat Scrape (Avg) | 26 | 19 | 21 | 16 |

EXAMPLE 11

In this example, the blocked isocyanate trimer prepared in example 1 was used as a crosslinking agent in Imidex ® esterimide wire enamel. Again, the enamel was applied to 18 AWG copper wire in seven passes on a 15 foot vertical tower. The properties of the cured enamel were also compared to the same enamel prepared with Mondur ®SH crosslinking agent. The results are set forth in Table IV.

TABLE IV

|  | Control |  | Example 11 |  |
|---|---|---|---|---|
| Speed (ft/min) | 50 | 65 | 50 | 65 |
| Surface | B+ | B+ | B+ | B+ |
| Continuity (Bks/300 ft) | 0 | 0 | 0 | 0 |
| Flexibility (25%+) | 2X | 1X | 1X | 1X |
| Dissipation Factor (at 220° C.) | 6.3 | 9.8 | 7.1 | 8.0 |
| Thermoplastic Flow | 402 | 389 | 413 | 370 |
| Heat Shock 0% | 1X | 1X | 1X | 1X |
| (30 min. @ 200° C.) 20% | 2X | 3X | 2X | 3X |
| Dielectric (KV) | 9.3 | 9.2 | 9.0 | 9.5 |
| Heat Age (0% 21 hrs. @ 175° C.) | 1X | 1X | 1X | 1X |
| Heat Age 100 hr. @ 200° C. Retained Dielectric (KV) | 9.5 | 8.9 | 10.2 | 9.8 |
| Repeat Scrape (Avg) | 34 | 31 | 31 | 19 |

We claim:

1. A method for making blocked isocyanate trimers, comprising:
   (A) blocking
      (1) one of the functional groups of an organic diisocyanate with
      (2) at least one blocking compound and thereafter
   (B) heating the reaction product of (A) in the presence of
      (3) a catalyst having the general formula

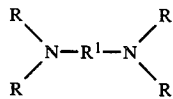

where each R is independently selected from hydrogen and lower alkyl radicals and $R^1$ is an alkylene radical having up to about six carbon atoms; for an amount of time effective for forming blocked isocyanate trimers.

2. A method for making blocked isocyanate trimers, comprising:
   (A) heating
      (1) at least one organic diisocyanate in the present of
      (2) a catalyst having the general formula

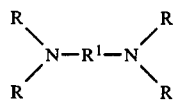

where each R is independently selected from hydrogen and lower alkyl radicals and $R^1$ is an alkylene radical having up to about six carbon atoms; for an amount of time effective for forming isocyanate trimers, and thereafter
   (B) blocking the isocyanate trimers prepared in step (A) with
      (3) a blocking compound.

3. A method as in claims 1 or 2, wherein the organic diisocyanate is selected from the group consisting of 1-alkylbenzene-2,4-diisocyanate, 1-alkylbenzene-2,5-diisocyanate, 1-alkylbenzene-2,6-diisocyanate, hexamethylene diisocyanate, diphenylmethane-4,4'-diisocyanate, and dicyclohexyl methane diisocyanate.

4. A method as in claim 3, wherein the organic diisocyanate is toluene diisocyanate.

5. A method as in claims 1 or 2, wherein the blocking compound is a monohydroxy compound.

6. A method as in claim 5, wherein the monohydroxy compound is selected from the group consisting of phenol, cresols and cyclohexanol.

7. A method as in claim 6, wherein the monohydroxy compound is phenol.

8. A method as in claim 4, wherein the monohydroxy compound is phenol.

9. A method as in claims 1 or 2, wherein each R is independently selected from methyl, ethyl and propyl and $R^1$ is an alkylene radical having from 2 to 4 carbon atoms.

10. A method as in claim 9, wherein the catalyst is tetramethylethylenediamine.

11. A method as in claim 4, wherein the catalyst is tetramethylethylenediamine.

12. A method as in claim 7, wherein the catalyst is tetramethylethylenediamine.

13. A method as in claim 1 or 2, wherein the catalyst is present in an amount of from about 0.05% to about 5% by weight based on the weight of organic diisocyanate and blocking compound.

14. A method as in claim 10, wherein the catalyst is present in an amount of from about 0.05% to about 5% by weight based on the weight of organic diisocyanate and blocking compound.

15. A method as in claim 13, wherein the catalyst is present in an amount of from about 0.10% to about 0.50% by weight based on the weight of organic diisocyanate and blocking agent.

16. A method as in claim 14, wherein the catalyst is present in an amount of from about 0.10% to about 0.50% by weight based on the weight of organic diisocyanate and blocking agent.

17. A method as in claims 1 or 2, wherein reaction is effected in a solvent.

18. A method as in claims 1 or 2, wherein the blocking step is effected at a temperature of from about 80° C. to about 160° C.

19. A method as in claim 18, wherein the trimerization step is carried out at a temperature of from about 80° C. to about 175° C.

20. A method as in claim 1 or 2, wherein the blocking step is effected at a temperature of from about 90° C. to about 120° C.

21. A method as in claim 20, wherein the trimerization step is carried out at a temperature of from about 90° C. to about 120° C.

22. A method as in claim 20, wherein the trimerization step is carried out at a temperature of from about 90° C. to about 100° C.

* * * * *